US012653232B2

(12) United States Patent
Reevell

(10) Patent No.: US 12,653,232 B2
(45) Date of Patent: Jun. 16, 2026

(54) AEROSOL GENERATING DEVICE WITH SECURING MEANS

(71) Applicant: Philip Morris Products S.A., Neuchatel (CH)

(72) Inventor: Tony Reevell, London (GB)

(73) Assignee: Philip Morris Products S.A., Neuchatel (CH)

( * ) Notice: Subject to any disclaimer, the term of this patent is extended or adjusted under 35 U.S.C. 154(b) by 626 days.

(21) Appl. No.: 17/838,899

(22) Filed: Jun. 13, 2022

(65) Prior Publication Data

US 2022/0304376 A1 Sep. 29, 2022

Related U.S. Application Data

(63) Continuation of application No. 16/093,340, filed as application No. PCT/EP2017/057781 on Mar. 31, 2017, now Pat. No. 11,388,929.

(30) Foreign Application Priority Data

Apr. 27, 2016 (EP) ..................................... 16167325

(51) Int. Cl.
*A24F 40/40* (2020.01)
*A24F 40/20* (2020.01)
(Continued)

(52) U.S. Cl.
CPC .............. *A24F 40/40* (2020.01); *A24F 40/20* (2020.01); *A61M 15/06* (2013.01); *H05B 6/02* (2013.01)

(58) Field of Classification Search
CPC .......... A24F 40/00; A24F 40/20; A24F 40/40; A24F 40/42; A24F 40/46; A24F 40/60; A61M 15/06
(Continued)

(56) References Cited

U.S. PATENT DOCUMENTS 5,505,214 A * 4/1996 Collins ................... H05B 3/24
131/194
2002/0032069 A1* 3/2002 Arrison ................ B43K 23/016
473/36
(Continued)

FOREIGN PATENT DOCUMENTS

CN 2892335 Y 4/2007
CN 203466240 U 3/2014
(Continued)

OTHER PUBLICATIONS

KR10-0304044 (Machine Translation) [online], [retrieved on Oct. 29, 2024], retrieved from google patents (https://patents.google.com/) (Year: 2001).*
(Continued)

*Primary Examiner* — Philip Y Louie
*Assistant Examiner* — Yana B Krinker
(74) *Attorney, Agent, or Firm* — Oblon, McClelland, Maier & Neustadt, L.L.P.

(57) ABSTRACT

An aerosol-generating device is provided, including: a housing defining a cavity configured to receive an aerosol-generating article, the cavity having an open end through which the aerosol-generating article is receivable into the cavity; and a constricting member connected to the housing, in which the constricting member is moveable between an open position and a constricting position, which selectively constricts at least a portion of the cavity, and in which the constricting member extends around at least part of an outside of the cavity of the housing.

8 Claims, 7 Drawing Sheets

(51) Int. Cl.
    *A61M 15/06*       (2006.01)
    *H05B 6/02*        (2006.01)

(58) Field of Classification Search
    USPC ........................................................ 131/273
    See application file for complete search history.

(56) References Cited

U.S. PATENT DOCUMENTS

| | | | |
|---|---|---|---|
| 2007/0235027 A1 | 10/2007 | Schuckmann | |
| 2007/0293826 A1 | 12/2007 | Wall et al. | |
| 2014/0305449 A1 | 10/2014 | Plojoux et al. | |
| 2014/0345606 A1* | 11/2014 | Talon ................ | A61M 16/0003 |
| | | | 128/203.14 |
| 2015/0013696 A1 | 1/2015 | Plojoux et al. | |
| 2015/0181936 A1 | 7/2015 | Lyubomirskiy et al. | |
| 2015/0272211 A1 | 10/2015 | Chung | |
| 2017/0119054 A1 | 5/2017 | Zinovik et al. | |

FOREIGN PATENT DOCUMENTS

| | | | |
|---|---|---|---|
| CN | 203723440 U | | 7/2014 |
| CN | 103987286 A | | 8/2014 |
| CN | 103997922 A | | 8/2014 |
| CN | 104135881 A | | 11/2014 |
| CN | 104770878 A | * | 7/2015 |
| CN | 205072071 U | | 3/2016 |
| JP | 3-114461 A | | 5/1991 |
| JP | 5-65343 U | | 8/1993 |
| JP | 7-184627 A | | 7/1995 |
| JP | 7-285005 A | | 10/1995 |
| JP | 8-11010 A | | 1/1996 |
| JP | 2010-509963 A | | 4/2010 |
| JP | 2014-501120 A | | 1/2014 |
| JP | 2014-533513 A | | 12/2014 |
| JP | 2015-506170 A | | 3/2015 |
| KR | 20-1998-001 4360 U | | 6/1998 |
| KR | 10-0304044 | * | 11/2001 |
| KR | 10-0304044 B1 | | 11/2001 |
| KR | 10-2009-0017100 A | | 2/2009 |
| KR | 10-2014-0093694 A | | 7/2014 |
| KR | 10-2015-0046605 A | | 4/2015 |
| WO | 2013/076098 A2 | | 5/2013 |
| WO | 2013/098395 A1 | | 7/2013 |
| WO | 2015/149406 A1 | | 10/2015 |
| WO | 2015/177254 A1 | | 11/2015 |
| WO | WO 2016/026810 A1 | | 2/2016 |

OTHER PUBLICATIONS

CN104770878A (Machine Translation) [online], [retrieved on Oct. 29, 2024], retrieved from ESPACENET (https://worldwide.espacenet.com/) (Year: 2015).*

Korean Office Action issued on Mar. 20, 2023 in Korean Patent Application No. 10-2022-7033220 (with English translation), 10 pages.

International Search Report and Written Opinion issued Jun. 9, 2017 in PCT/EP2017/057781, filed Mar. 31, 2017.

Extended European Search Report issued Nov. 4, 2016 in Patent Application No. 16167325.6.

Combined Russian Office Action and Search Report issued on May 25, 2020, in Patent Application No. 2018141381, 17 pages (with English translation).

Combined Chinese Office Action and Search Report issued Dec. 25, 2020 in Patent Application No. 201780022711.0 (with English language translation), 14 pages.

Japanese Office Action issued Mar. 15, 2021 in Japanese Patent Application No. 2018-554564 (with English translation), 11 pages.

Korean Office Action issued Dec. 17, 2021 in Korean Patent Application No. 10-2018-7030164 (with English translation), 12 pages.

CN-104770878-A (Machine Translation) [online], [retrieved on Aug. 9, 2021], retrieved from google patents (https://patents.google.com/) (Year: 2015).

Combined Chinese Office Action and Search Report issued Nov. 6, 2023 in Chinese Patent Application No. 202210310527.9 (with English Translation), 12 pages.

Japanese Office Action dated Jun. 17. 2024 in corresponding Japanese Patent Application No. 2023-062727 (with English translation), 8 pages.

\* cited by examiner

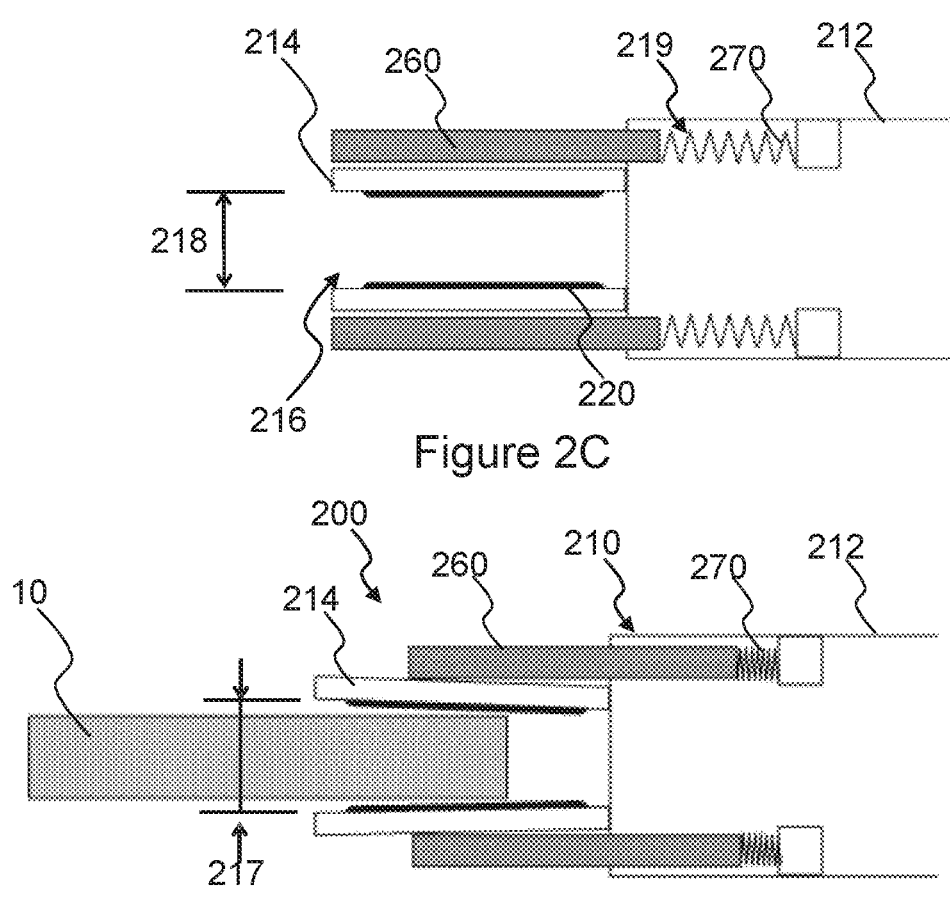
Figure 2C
Figure 2D
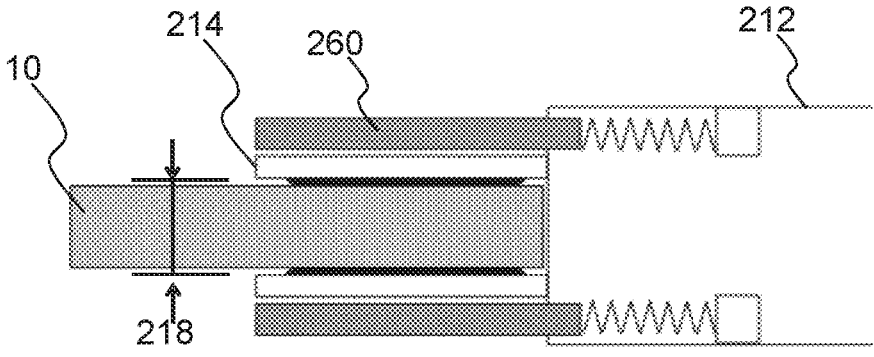
Figure 2E

AEROSOL GENERATING DEVICE WITH SECURING MEANS

CROSS-REFERENCE TO RELATED APPLICATIONS

This application is a continuation of and claims benefit under 35 U.S.C. § 120 to U.S. application Ser. No. 16/093,340, filed on Oct. 12, 2018, which is a U.S. National Stage application of PCT/EP2017/057781, filed on Mar. 31, 2017, and claims the benefit of priority under 35 U.S.C. § 119 to European Application No. 16167325.6, filed on Apr. 27, 2016, the entire contents of each of which are incorporated herein by reference.

TECHNICAL FIELD

The present invention relates to an aerosol-generating device for use in an aerosol-generating system and to aerosol-generating systems comprising the aerosol-generating device.

DESCRIPTION OF THE RELATED ART

One type of aerosol-generating system is an electrically operated system typically comprising an aerosol-generating device including a battery, control electronics and an electric heater, and an aerosol-generating article designed specifically for use with the aerosol-generating device. In some examples, the aerosol-generating article comprises an aerosol-generating substrate, such as a tobacco rod or a tobacco plug, and the heater contained within the aerosol-generating device is inserted into or around the aerosol-generating substrate when the aerosol-generating article is inserted into the aerosol-generating device. In an alternative electrically operated system, the aerosol-generating article may comprise a capsule containing an aerosol-generating substrate, such as loose tobacco.

Typically, an aerosol-generating device is reusable with a plurality of disposable or refillable aerosol-generating articles. When the aerosol-generating article is inserted into the aerosol-generating device, the relative position of the aerosol-generating article and the heater can be important for consistent aerosol characteristics. Additionally, the ease with which the aerosol-generating article is inserted into, or removed from, the aerosol-generating device is also important to avoid difficulty for the user and may reduce the risk of damage to the aerosol-generating article when it is inserted into the aerosol-generating device.

Accordingly, it would be desirable to provide an aerosol-generating device which allows secure holding of an aerosol-generating article without undue burden on the user when inserting the aerosol-generating article into the aerosol-generating device.

SUMMARY

According to a first aspect of the present invention there is provided an aerosol-generating device comprising: a housing defining a cavity for receiving an aerosol-generating article, the cavity having an open end through which the article is receivable into the cavity; and a constricting member connected to the housing, wherein the constricting member is moveable between an open position and a constricting position to selectively constrict at least a portion of the cavity.

According to a second aspect of the present invention there is provided an aerosol-generating system comprising an aerosol-generating article and an aerosol-generating device according to the first aspect of the present invention, in accordance with any of the embodiments described above. The aerosol-generating article comprises an aerosol-forming substrate that is vaporised, during use, by the aerosol-generating device to form an aerosol.

BRIEF DESCRIPTION OF THE DRAWINGS

The invention is further described, by way of example only, with reference to the accompanying drawings in which:

FIGS. 1B and 1C are perspective views of the aerosol-generating device of FIG. 1A, in which FIG. 1B shows the constricting member in the open position and FIG. 1C shows the constricting member in the constricting position;

FIGS. 1D to 1F are schematic longitudinal cross-section views of the upstream end of the aerosol-generating device of FIGS. 1A to 1C, in which FIG. 1D shows the constricting member in the constricting position prior to insertion of an aerosol-generating article into the cavity, FIG. 1E shows the constricting member in the open position during insertion of an aerosol-generating article in the cavity, and FIG. 1F shows the constricting member in the constricting position following insertion of an aerosol-generating article into the cavity;

FIGS. 2A and 2B are perspective views of an aerosol-generating device in accordance with a second embodiment of the present invention, in which FIG. 2A shows the constricting member in the open position and FIG. 2B shows the constricting member in the constricting position;

FIGS. 2C to 2E are schematic longitudinal cross-section views of the upstream end of the aerosol-generating device of FIGS. 2A and 2B, in which FIG. 2C shows the constricting member in the constricting position prior to insertion of an aerosol-generating article into the cavity, FIG. 2D shows the constricting member in the open position during insertion of an aerosol-generating article in the cavity, and FIG. 2E shows the constricting member in the constricting position following insertion of an aerosol-generating article into the cavity;

FIGS. 3A and 3B are perspective views of an aerosol-generating device in accordance with a third embodiment of the present invention, in which FIG. 3A shows the constricting member in the open position and FIG. 3B shows the constricting member in the constricting position; and FIGS. 3C to 3E are schematic longitudinal cross-section views of the upstream end of the aerosol-generating device of FIGS. 3A and 3B, in which FIG. 3C shows the constricting member in the constricting position prior to insertion of an aerosol-generating article into the cavity, FIG. 3D shows the constricting member in the open position during insertion of an aerosol-generating article in the cavity, and FIG. 3E shows the constricting member in the constricting position following insertion of an aerosol-generating article into the cavity.

DETAILED DESCRIPTION

Figure 1A:
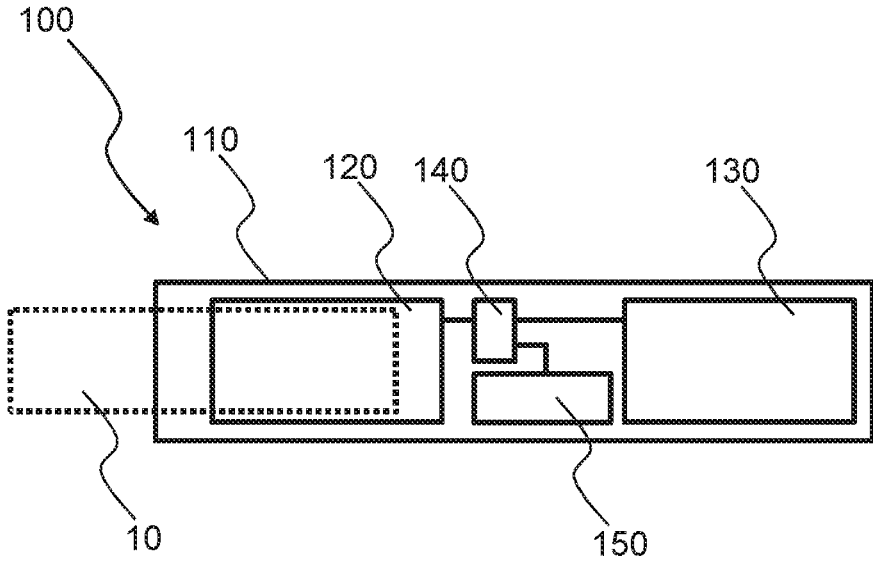
FIG. 1A shows a schematic diagram of an aerosol-generating device in accordance with a first embodiment of the present invention.

Advantageously, aerosol-generating devices according to the present invention provide a simple way for a user to insert, grip and remove an aerosol-generating article. When the constricting member is in the open position, an aerosol-forming substrate may be easily inserted into and removed from the cavity. When the constricting member is in the constricting position, the minimum diameter of the cavity is reduced such that an aerosol-generating article may be securely gripped by the device and held in position within the cavity. This avoids the need for a compromise between secure gripping of an aerosol-generating article by the aerosol-generating device and easy insertion of the aerosol-generating article into the aerosol-generating device, as may be the case with other devices. The constricting member remains connected to the housing regardless of whether it is in the constricting member or in the open position. Thus, no removal of the constricting member from the housing is necessary in order to insert an aerosol-generating article into the cavity.

The terms "constrict" and "constricting" are used herein to refer to a reduction in the minimum diameter of the cavity. That is, a reduction in the minimum dimension of the cavity in the transverse direction of the aerosol-generating device.

In preferred examples, the terms "constrict" and "constricting" refer to a reduction in the minimum diameter of the cavity of at least 2 percent, at least 5 percent, at least 10 percent, or at least 20 percent. In these examples, the minimum diameter of the cavity is preferably reduced by no more than 50 percent.

In preferred examples, the constricting member is selectively moveable between the open position and the constricting position when the aerosol-generating article is received in the cavity to selectively constrict at least a portion of the cavity.

In preferred examples, when the constricting member is in the open position, the minimum diameter of the cavity is equal to or greater than the maximum outer diameter of aerosol-generating articles used with the device, preferably greater than. When the constricting member is in the constricting position, the minimum diameter of the cavity should be less than or equal to the maximum outer diameter of aerosol-generating articles used with the device, preferably less than. In any configuration, the minimum diameter of the cavity when the constricting member is in the open position is greater than the minimum diameter of the cavity when the constricting member is in the constricting position When the constricting member is in the open position, the minimum diameter of the cavity is equal to or greater than the maximum outer diameter of the aerosol-generating article, preferably slightly greater. When the constricting member is in the constricting position, the minimum diameter of the cavity is equal to or less than the maximum outer diameter of the aerosol-generating article, preferably slightly less than. In any configuration, the minimum diameter of the cavity is relatively greater when the constricting member is in the open position than when it is in the closed position.

The constricting member may be freely moveable between the open position and the constricting position. This means that the constricting member will generally remain in the position to which it was last moved by a user. In such examples, the constricting member may moved manually by the user between the open position and the constricting position, and vice versa.

When in the constricting position, the constricting member may be arranged to constrict the cavity at any suitable location along the length of the cavity. That is, at any location along the length of the cavity which is adjacent to the aerosol-generating article when fully inserted into the cavity. In preferred examples, the constricting member is moveable between an open position and a constricting position to selectively constrict the open end of the cavity. This allows the constricting member to provide a particularly secure grip on the aerosol-generating article.

In certain preferred embodiments, the constricting member is biased towards the constricting position. This means that the constricting member will automatically move from the open position to the constricting position without user interaction. With this arrangement, the constricting member is held in the constricting position unless moved to the open position by a user. Advantageously, this allows the aerosol-generating device to securely grip an aerosol-generating article without requiring the user to manually move the constricting member from the open position to the constricting position once the aerosol-generating article has been received in the cavity. It may also reduce the chance of the constricting member being moved unintentionally from the constricting position to the open position, for example if the device is accidentally knocked during use.

The constricting member may be biased towards the constricting position by any suitable mechanism. For example, the constricting member and a portion of the housing, for example at the open end of the cavity, may be co-operatively shaped such that a restoring force is applied by the housing to the constricting member when the constricting member is in the open position to bias the constricting member towards the constricting position. One or both of the constricting member and a portion of the housing, for example at the open end of the cavity, may be elastically deformed when the constricting member is in the open position, whereby the elastic deformation provides the restoring force to bias the constricting member towards the constricting position.

Aerosol-generating devices according to the present invention may further comprise a spring between the housing and the constricting member, wherein the spring is arranged to bias the constricting member towards the constricting position.

In certain embodiments, the constricting member comprises a collar extending around the outside of the cavity of the housing. Advantageously, this may provide a particularly robust arrangement. In such embodiments, the collar may extend around an outer surface of the housing, for example around an outer surface of a wall of the housing which defines the cavity. Alternatively, or in addition, part of or all of the collar may be received in a recess or cavity in the housing.

In other examples, the constricting member may extend only partially around the outside of the cavity or the housing, or partially around part of the outside of the cavity or the housing, for example the open end of the cavity. For example, the constricting member may comprise a C-shaped member, or a finger, arm, or other, similar element that is moveable to constrict the cavity, for example by constricting the open end of the cavity.

In any of the above embodiments, the constricting member may be slidably connected to the housing such that it is moveable along the length of the housing. Advantageously, this may result in a compact, simple arrangement. In one particular example, the constricting member comprises a collar extending around the housing and is slidably connected to the housing such that it is moveable along a region of the length of the housing.

In other examples, the constricting member may be pivotally connected to the housing so that it is moveable between the open and constricting positions by a pivoting action. In yet further examples, the constricting member may be rotatable relative to the housing so that it is moveable between the open and constricting positions by rotation. For example, the constricting member may be connected to the housing via a threaded connection so that rotation of the constricting member causes it to move relative to the housing along the axial direction of the threaded connection. In such examples, the axial direction of the threaded connection may be substantially parallel or aligned with the longitudinal axis of the housing so that the constricting member is moveable along the length of the housing upon rotation of the constricting member on the threaded connection In embodiments in which the constricting member is moveable along a region of the length of the housing, the housing preferably further comprises a recess for receiving at least part of the constricting member when the constricting member is in the open position. With this arrangement, the constricting member is able to extend into the recess when moved to the open position. Advantageously, this may reduce interference between the constricting member and the user's grip on the device in comparison to arrangements in which the constricting member moves only along the outer surface of the housing. This allows the size of the constricting member to be increased to allow for easier handling of the constricting member without adversely affecting the user's grip on the housing. In some embodiments, the constricting member is slidably connected to the housing such that it is moveable along at least a region of the length of the housing, and the housing further comprises a recess for receiving at least part of the constricting member when the constricting member is in the open position.

In other examples, the constricting member is moveable along the length of the housing and over the outer surface of the housing such that the constricting member is outside of the housing in both the constricting and open positions.

In any of the above embodiments, the housing preferably comprises a main body and a moveable wall connected to the main body, the moveable wall defining at least part of the open end of the cavity, wherein the moveable wall is moveable between a first position in which the open end has a first minimum diameter and a second position in which the open end has a second, smaller minimum diameter, and wherein the constricting member is arranged to selectively constrict the open end of the cavity by deflecting the moveable wall to the second position. With this arrangement, the minimum diameter of the open end of the cavity is defined by the moveable wall and the open end of the cavity may be constricted indirectly by the constricting member via the moveable wall. In other examples, the minimum diameter of the open end of the cavity may be defined by the constricting member and the constricting member arranged to selectively constrict the open end of the cavity directly.

As used herein, the term "moveable wall" refers to a portion of the housing forming a side wall defining part of the cavity, which is configured for movement relative to the main body of the housing.

The moveable wall preferably defines the entire open end of the cavity. In other words, the moveable wall may extend around the entire circumference of the cavity at its open end. In such embodiments, the moveable wall may extends around the circumference of the cavity in a continuous or discontinuous manner. Where the moveable wall is discontinuous, it may extend around the entire circumference of the open end of the cavity as a plurality of sections each separated from adjacent sections by a narrow gap. In other embodiments, the moveable wall may extend only part of the way around the circumference of the cavity, with the reminder of the cavity being defined by one or more additional wall sections which may be fixed or moveable relative to the main body of the housing.

In some examples, the moveable wall defines only the open end of the cavity. In such examples, the remainder of the cavity may defined by one or more additional wall sections which may be fixed or moveable relative to the main body. In other examples, the moveable wall defines both the open end of the cavity and the side walls of the cavity, along at least part of the length of the cavity. In one particular example, the moveable wall defines the open end of the cavity and the side walls of the cavity along substantially the entire length of the cavity.

The moveable wall may be formed from a single, unitary component. In other examples, the moveable wall may be formed from a plurality of components. For example, the moveable wall may be formed from a plurality of walls or pivotally mounted blades or leaves, such as iris blades, arranged around the open end of the cavity.

The moveable wall may be biased towards the first position when the constricting member is in the open position. Advantageously, with this arrangement, the moveable wall automatically moves to the first position to enlarge the open end of the cavity when the constricting member is moved to the open position, reducing the burden on the user.

In preferred embodiments, the moveable wall is resilient and arranged to deflect relative to the main body of the housing to move to the second position by elastic deformation when the constricting member is moved to the constricting position and to return automatically to the first position when the constricting member is moved to the open position. This provides a simple and robust means by which the moveable wall may be biased towards the first position to allow for easy insertion or removal of an aerosol-generating article.

In such embodiments, the moveable wall may be fixed to the main body of the housing so that movement between the first and second positions is solely by deformation.

The moveable wall may be connected to the main body of the housing by a hinge about which the moveable wall is moveable between the first and second positions.

The aerosol-generating device is preferably an electrically heated aerosol-generating device and further comprises an electric heater. In such examples, the electric heater is preferably positioned in the cavity for heating an aerosol-forming substrate when received in the cavity.

The electric heater may comprise one or more external heating elements, one or more internal heating elements, or one or more external heating elements and one or more internal heating elements. As used herein, the term "external heating element" refers to a heating element that is positioned outside the aerosol-forming substrate of an aerosol-generating article received in the cavity. As used herein, the term "internal heating element" refers to a heating element that is positioned at least partially within the aerosol-forming substrate of an aerosol-generating article received in the cavity. The at least one external heating element may comprise an array of external heating elements arranged around the periphery of the cavity, for example on a side wall of the housing. In certain examples, the external heating elements extend along the longitudinal direction of the cavity. With this arrangement, the heating elements extend along the same direction in which an aerosol-generating article is inserted into and removed from the cavity. This may reduce interference between the heating elements and the aerosol-generating article when the article is inserted into and removed from the cavity relative to devices in which the heating elements are not aligned with the length of the cavity. In some embodiments, the external heating elements extend along the length direction of the cavity and are spaced apart in the circumferential direction. Where the electric heater comprises at least one internal heating element, the heating element may comprise any suitable number of heating elements. For example, the heater may comprise a single internal heating element. The single internal heating element may extend along the longitudinal direction of the cavity.

Preferably, the aerosol-generating device is portable. The aerosol-generating device may have a size comparable to a conventional cigar or cigarette. The aerosol-generating device may have a total length between approximately 30 mm and approximately 150 mm. The aerosol-generating device may have an external diameter between approximately 5 mm and approximately 30 mm.

Where the aerosol-generating device comprises an electric heater, the aerosol-generating device may further comprise a power supply for powering the electric heater. In such embodiments, the housing may define at least one internal compartment in which the power supply is located. The at least one internal compartment may be separate from the cavity. The cavity may form part of the at least one internal compartment.

The power supply may be a battery, such as a rechargeable lithium ion battery. Alternatively, the power supply may be another form of charge storage device such as a capacitor. The power supply may require recharging. The power supply may have a capacity that allows for the storage of enough energy for one or more substrate inhalation experiences. For example, the power supply may have sufficient capacity to allow for the continuous generation of aerosol for a period of around six minutes, corresponding to the typical time taken to smoke a conventional cigarette, or for a period that is a multiple of six minutes. In another example, the power supply may have sufficient capacity to allow for a predetermined number of puffs or discrete activations of the electric heater.

In any of the embodiments described above, the aerosol-generating device may comprise an electric heater configured to heat an aerosol-forming substrate to produce an aerosol. The electric heater comprises at least one heating element and may be configured to heat a solid aerosol-forming substrate or a liquid aerosol-forming substrate. The at least one heating element may comprise one or more resistive heating elements. The at least one heating element may comprise one or more inductive heating elements. The at least one heating element may comprise one or more resistive heating elements and one or more inductive heating elements. The aerosol-generating device may further comprise a controller configured to control the supply of power to the heater. The controller may be configured to disable operation of the device by preventing the supply of power to the electric heater and may enable operation of the device by allowing the supply of power to the electric heater.

The at least one electric heating element preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver Colo. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company, 1007 Market Street, Wilmington, Delaware 19898, United States of America.

The at least one electric heating element may comprise an infra-red heating element, a photonic source, or an inductive heating element.

The at least one electric heating element may take any suitable form. For example, the at least one electric heating element may take the form of a heating blade. The at least one electric heating element may take the form of a casing or substrate having different electro-conductive portions, or an electrically resistive metallic tube. If the aerosol-forming substrate is a liquid provided within a container, the container may incorporate a disposable heating element. One or more heating needles or rods that run through the centre of the aerosol-forming substrate may be used. The at least one electric heating element may be a disk (end) heating element or a combination of a disk heating element with heating needles or rods. The at least one electric heating element may comprise a flexible sheet of material arranged to surround or partially surround the aerosol-forming substrate. Other possibilities include a heating wire or filament, for example a Ni—Cr, platinum, tungsten or alloy wire, or a heating plate. Optionally, the heating element may be deposited in or on a rigid carrier material.

The at least one electric heating element may comprise a heat sink, or heat reservoir comprising a material capable of absorbing and storing heat and subsequently releasing the heat over time to the aerosol-forming substrate. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable heat storage materials include silica gel, alumina, carbon, glass mat, glass fibre, minerals, a metal or alloy such as aluminium, silver or lead, and a cellulose material such as paper. Other materials which release heat via a reversible phase change include paraffin, sodium acetate, naphthalene, wax, polyethylene oxide, a metal, metal salt, a mixture of eutectic salts or an alloy.

The heat sink or heat reservoir may be arranged such that it is directly in contact with the aerosol-forming substrate and can transfer the stored heat directly to the substrate. The heat stored in the heat sink or heat reservoir may be transferred to the aerosol-forming substrate by means of a heat conductor, such as a metallic tube.

The at least one heating element may heat the aerosol-forming substrate by conduction. The heating element may be at least partially in contact with the substrate, or a carrier on which the substrate is deposited. The heat from the heating element may be conducted to the substrate by a heat conductive element.

The at least one heating element may transfer heat to the incoming ambient air that is drawn through the electrically heated aerosol generating device during use, which in turn heats the aerosol-forming substrate by convection. The ambient air may be heated before passing through the aerosol-forming substrate. If the aerosol-forming substrate is a liquid substrate, the ambient air may be first drawn through the substrate and then heated.

The at least one heating element may comprise an inductive heating element, such that, where the device forms part of an aerosol-generating system consisting of the aerosol generating device and a removable aerosol-generating article, no electrical contacts are formed between the article and the device. The device may comprise an inductor coil and a power supply configured to provide high frequency oscillating current to the inductor coil. The article may comprise a susceptor element positioned to heat the aerosol-forming substrate. As used herein, a high frequency oscillating current means an oscillating current having a frequency of between 500 kHz and 10 MHz.

The housing may be elongate. The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

The housing may comprise a mouthpiece. The mouthpiece may comprise at least one air inlet and at least one air outlet. The mouthpiece may comprise more than one air inlet. One or more of the air inlets may reduce the temperature of the aerosol before it is delivered to a user and may reduce the concentration of the aerosol before it is delivered to a user. As used herein, the term "mouthpiece" refers to a portion of an aerosol-generating device that is placed into a user's mouth in order to directly inhale an aerosol generated by the aerosol-generating device from an aerosol-generating article received in the cavity of the housing.

As used herein, the term 'aerosol-forming substrate' relates to a substrate capable of releasing volatile compounds that can form an aerosol. Such volatile compounds may be released by heating the aerosol-forming substrate. An aerosol-forming substrate may conveniently be part of an aerosol-generating article.

As used herein, the term 'aerosol-generating article' refers to an article comprising an aerosol-forming substrate that is capable of releasing volatile compounds that can form an aerosol. For example, an aerosol-generating article may be an article that generates an aerosol that is directly inhalable into a user's lungs by the using drawing or puffing on a mouthpiece at a proximal or user-end of the system. An aerosol-generating article may be disposable. An article comprising an aerosol-forming substrate comprising tobacco is referred to as a tobacco stick.

As used herein, the term "aerosol-generating device" refers to a device that interacts with an aerosol-generating article to generate an aerosol.

When the constricting member is in the open position, the minimum diameter of the cavity is equal to or greater than the maximum outer diameter of the aerosol-generating article, preferably greater. When the constricting member is in the constricting position, the minimum diameter of the cavity is equal to or less than the maximum outer diameter of the aerosol-generating article, preferably less than. In any configuration, the minimum diameter of the cavity when the constricting member is in the open position is greater than the minimum diameter of the cavity when the constricting member is in the constricting position.

The aerosol-generating system may include a user interface to activate the system, for example a button to initiate heating of the device or display to indicate a state of the device or the aerosol-forming substrate.

The aerosol-generating system may be an electrically heated system that heats an aerosol-forming substrate to generate an aerosol. The aerosol-forming substrate may be a liquid, held in a liquid storage portion or may be a solid substrate. In either case, the aerosol-forming substrate may be provided in a replaceable, consumable portion that engages the device in use. The system may be a heated tobacco type system in which a cigarette is heated but not combusted to form an aerosol that can be directly inhaled by a user.

In preferred embodiments, the aerosol-generating system comprises an electric heater for heating the aerosol-forming substrate during use to produce an aerosol.

The electric heater may indirectly heat the aerosol-forming substrate. The electric heater may be an inductive heater and the aerosol-generating article may further comprise a susceptor in thermal communication with the aerosol-forming substrate. During use, the susceptor is heated by the inductive heater and the aerosol-forming substrate is heated by the susceptor. The susceptor may be configured to heat the aerosol-forming substrate by at least one of conductive heat transfer, convective heat transfer, radiative heat transfer, and combinations thereof.

The aerosol-generating article may be partially contained within the aerosol-generating device.

The aerosol-generating article may be substantially cylindrical in shape. The aerosol-generating article may be substantially elongate. The aerosol-generating article may have a length and a circumference substantially perpendicular to the length. The aerosol-forming substrate may be substantially cylindrical in shape. The aerosol-forming substrate may be substantially elongate. The aerosol-forming substrate may also have a length and a circumference substantially perpendicular to the length.

The aerosol-generating article may have a total length between approximately 30 mm and approximately 100 mm. In one embodiment, the aerosol-generating article has a total length of approximately 45 mm. The aerosol-generating article may have an external diameter between approximately 5 mm and approximately 12 mm. In one embodiment, the aerosol-generating article may have an external diameter of approximately 7.2 mm.

The aerosol-forming substrate may have a length of between about 7 mm and about 15 mm. In one embodiment, the aerosol-forming substrate may have a length of approximately 10 mm. Alternatively, the aerosol-forming substrate may have a length of approximately 12 mm.

The aerosol-generating substrate preferably has an external diameter that is approximately equal to the external diameter of the aerosol-generating article. The external diameter of the aerosol-forming substrate may be between approximately 5 mm and approximately 12 mm. In one embodiment, the aerosol-forming substrate may have an external diameter of approximately 7.2 mm.

The aerosol-generating article may comprise a filter plug. The filter plug may be located at a downstream end of the aerosol-generating article. The filter plug may be a cellulose acetate filter plug. The filter plug is approximately 7 mm in length in one embodiment, but may have a length of between approximately 5 mm to approximately 10 mm.

The aerosol-generating article may comprise an outer paper wrapper. Further, the aerosol-generating article may comprise a separation between the aerosol-forming substrate and the filter plug. The separation may be approximately 18 mm, but may be in the range of approximately 5 mm to approximately 25 mm.

The aerosol-forming substrate may be a solid aerosol-forming substrate. Alternatively, the aerosol-forming substrate may comprise both solid and liquid components. The aerosol-forming substrate may comprise a tobacco-containing material containing volatile tobacco flavour compounds which are released from the substrate upon heating. Alternatively, the aerosol-forming substrate may comprise a non-tobacco material. The aerosol-forming substrate may further comprise an aerosol former that facilitates the formation of a dense and stable aerosol. Examples of suitable aerosol formers are glycerine and propylene glycol.

In a particularly preferred embodiment, the aerosol-forming substrate comprises a gathered crimped sheet of homogenised tobacco material. As used herein, the term 'crimped sheet' denotes a sheet having a plurality of substantially parallel ridges or corrugations.

The aerosol-generating article may comprise a liquid storage portion and a liquid aerosol-forming substrate stored within the liquid storage portion. During use, the electric heater heats a small portion of the liquid aerosol-forming substrate in order to vaporize the small portion of the liquid aerosol-forming substrate. The liquid aerosol-forming substrate preferably comprises a tobacco-containing material comprising volatile tobacco flavour compounds which are released from the liquid upon heating. Alternatively, or in addition, the liquid aerosol-forming substrate may comprise a non-tobacco material. The liquid aerosol-forming substrate may include water, solvents, ethanol, plant extracts and natural or artificial flavours. Preferably, the liquid aerosol-forming substrate further comprises an aerosol former.

As used herein, the term 'aerosol former' is used to describe any suitable known compound or mixture of compounds that, in use, facilitates formation of an aerosol. Suitable aerosol formers are substantially resistant to thermal degradation at the operating temperature of the aerosol-generating article. Examples of suitable aerosol formers are glycerine and propylene glycol.

The aerosol-generating article may further comprise a capillary wick in communication with the liquid storage portion. The capillary wick is arranged to be in contact with the liquid aerosol-forming substrate within the liquid storage portion. During use, liquid aerosol-forming substrate is transferred from the liquid storage portion along the capillary wick by capillary action, where it is heated by the electric heater. In embodiments in which the electric heater comprises an inductive heater, the aerosol-generating article may further comprise a susceptor. During use, the inductive heater heats the susceptor and liquid aerosol-forming substrate is transferred from the liquid storage portion to the susceptor via the capillary wick.

The aerosol-generating system is a combination of an aerosol-generating device and one or more aerosol-generating articles for use with the device. However, aerosol-generating system may include additional components, such as for example a charging unit for recharging an on-board electric power supply in an electrically operated or electric aerosol-generating device.

Features described in relation to one or more aspects may equally be applied to other aspects of the invention. In particular, features described in relation to the device of the first aspect may be equally applied to the system of the second aspect, and vice versa.

Referring to FIG. 1A, the components of an electrically heated aerosol-generating device 100 according to a first embodiment of the present invention are shown in a simplified manner. Particularly, the elements of the electrically heated aerosol-generating device 100 are not drawn to scale in FIG. 1. Elements that are not relevant for the understanding of this device have been omitted to simplify FIG. 1A.

The electrically heated aerosol generating device 100 comprises a housing 110 defining a cavity for receiving an aerosol-generating article 10, for example a tobacco stick. The aerosol-forming article 10 includes an aerosol-forming substrate that is pushed inside the cavity of the housing 110 to come into thermal proximity with a heater 120. The aerosol-forming substrate will release a range of volatile compounds at different temperatures.

Within the housing 110 is an electrical energy supply 130, for example a rechargeable lithium ion battery. A controller 140 is connected to the heater 120, the electrical energy supply 130, and a user interface 150, for example a button to initiate heating of the device or display to indicate a state of the device or the aerosol-forming substrate. The controller 140 controls the power supplied to the heater 120 in order to regulate its temperature. Typically the aerosol-forming substrate is heated to a temperature of between 250 and 450 degrees centigrade. By controlling the maximum operation temperature of the electrically heated aerosol generating device 100 the release of undesirable volatile compounds may be controlled.

Referring to FIGS. 1B to 1F, the housing is formed from a main body 112 and a moveable wall 114 connected to the main body 112 and located at the upstream end of the device 100. The main body 112 houses the electrical energy supply, controller, and user interface. The moveable wall 114 defines the cavity 116 within which the aerosol-generating article 10 is receivable. The electric heater 120 is positioned in the cavity 116. In this example, the electric heater comprises an internal heating element in the form of a heater blade 120 arranged to penetrate an aerosol-generating article 10 received in the cavity 116 and to heat the aerosol-forming substrate from within.

Figure 1B:
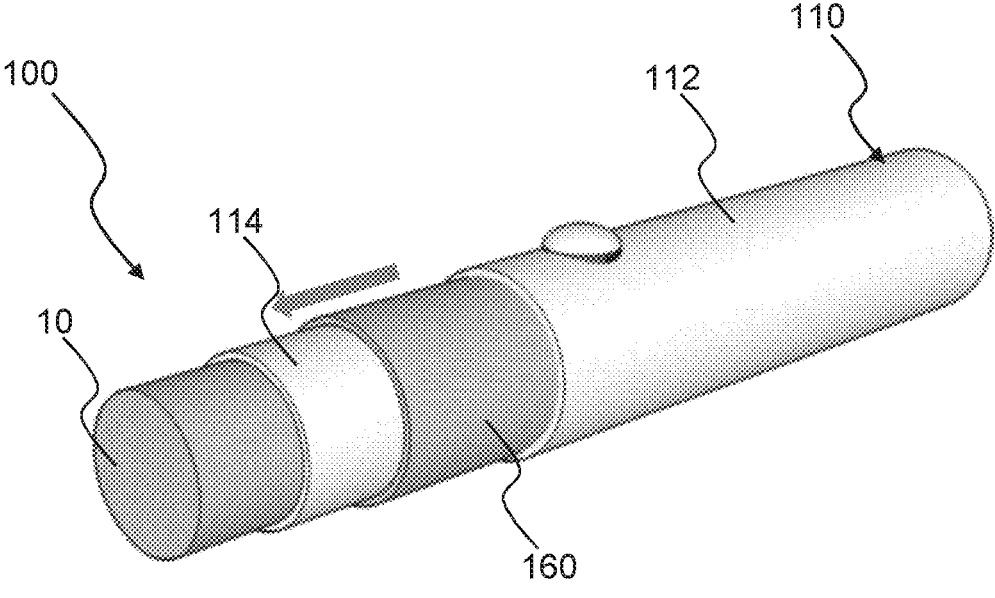
Figure 1C:
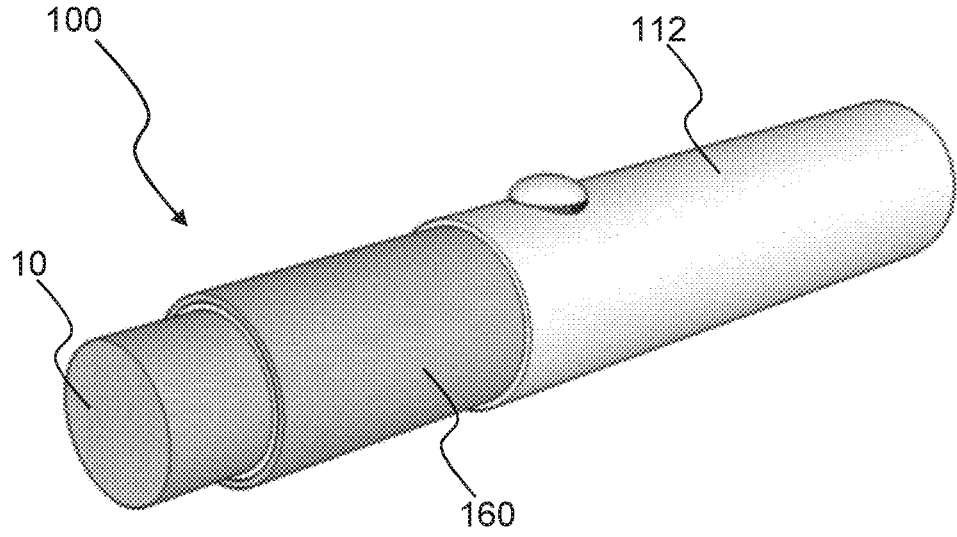

The aerosol-generating device 100 further comprises a constricting member in the form of a tubular collar 160 extending around the moveable wall 114 at the upstream end of the housing 110. The tubular collar 160 is slidably connected to the housing 110 such that it is moveable along the length of the housing 110 between an open position, as shown in FIG. 1B, and a constricting position, as shown in FIG. 1C. When in the open position, the downstream end of the collar 160 is received within a recess 119 in the main body 112 of the housing 110. The collar 160 is connected to the main body 112 of the housing 110 by a spring 170 which is arranged to bias the collar 160 towards the constricting position, as shown in FIG. 1C.

Figures 1D, 1E, 1F:
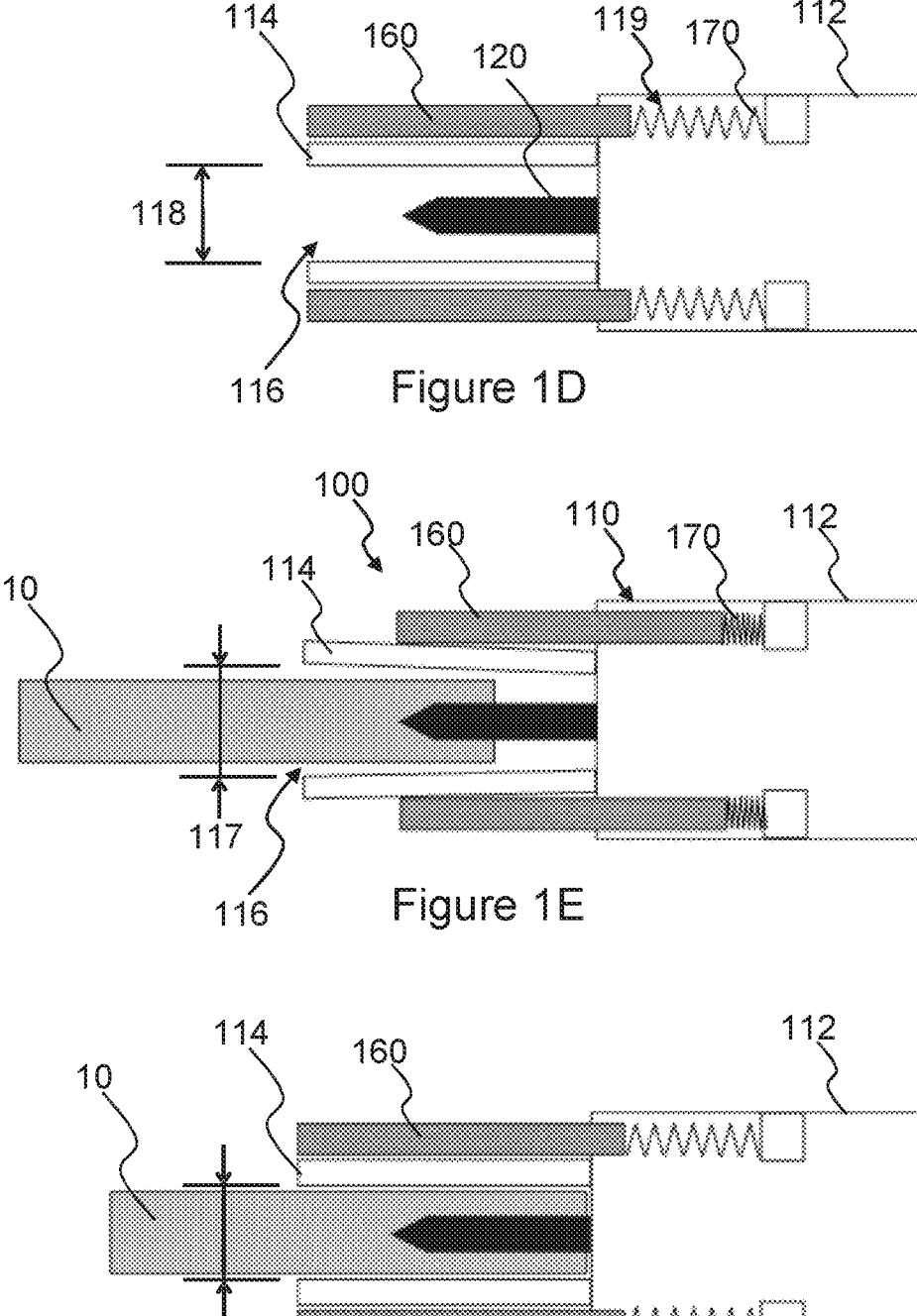
Figure 2A:
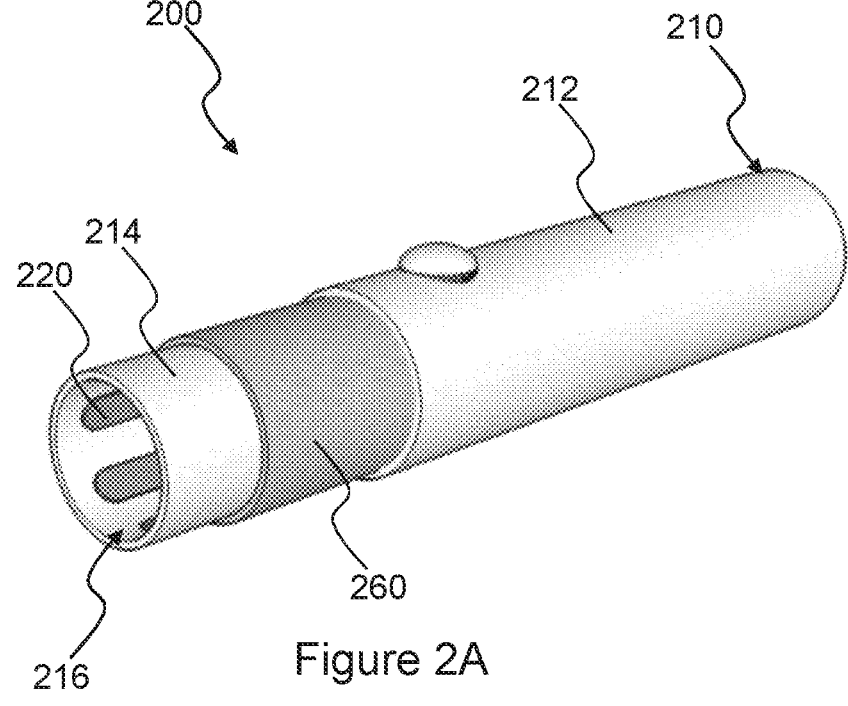
Figure 2B:
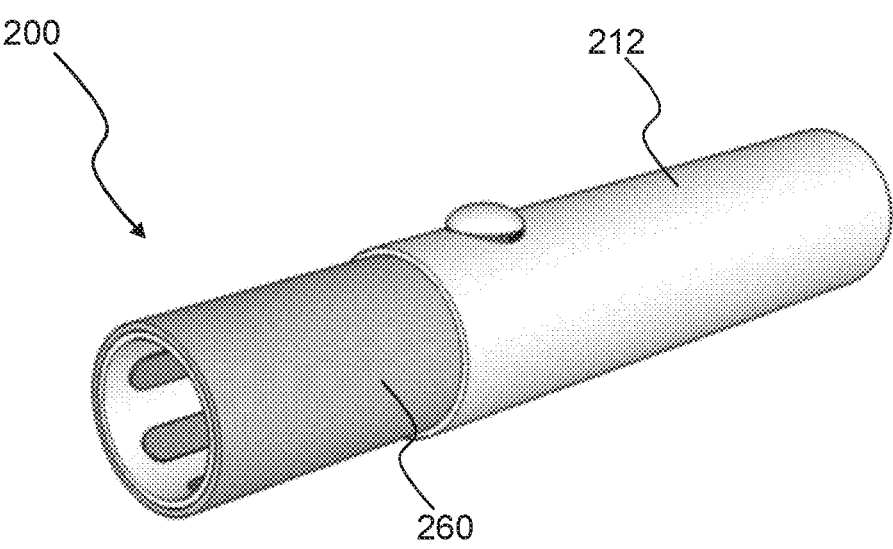
Figure 3A:
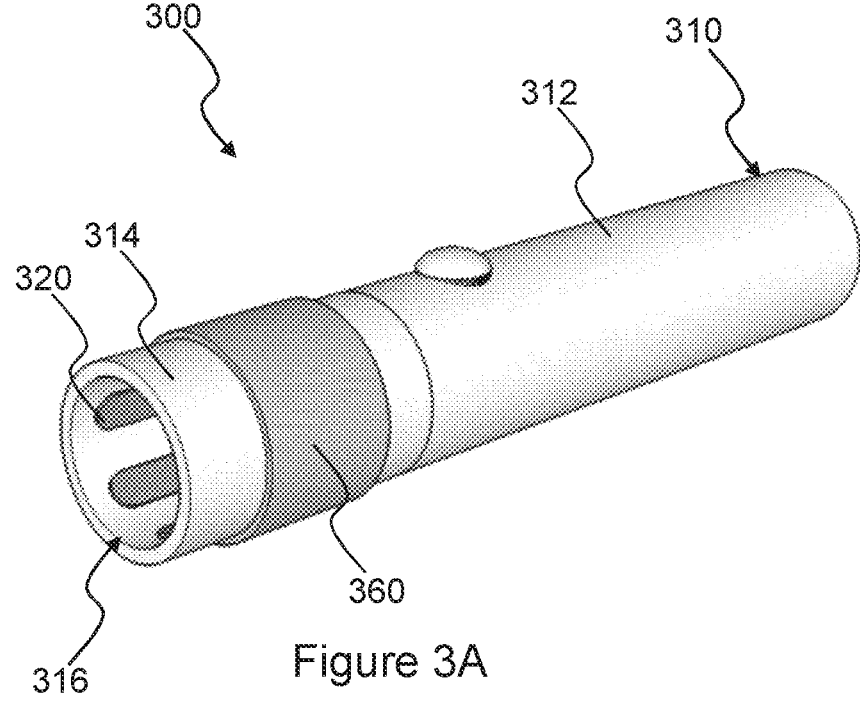
Figure 3B:
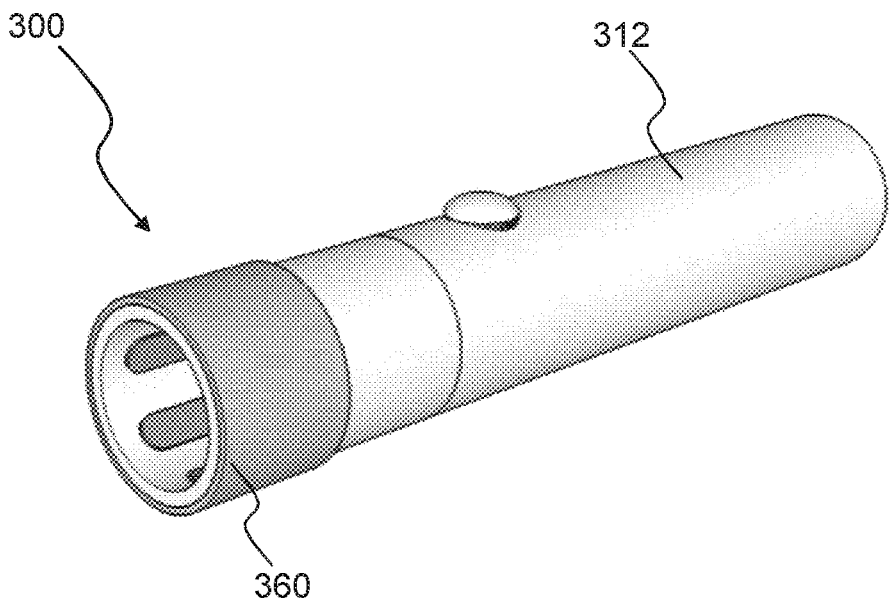
Figure 3C:
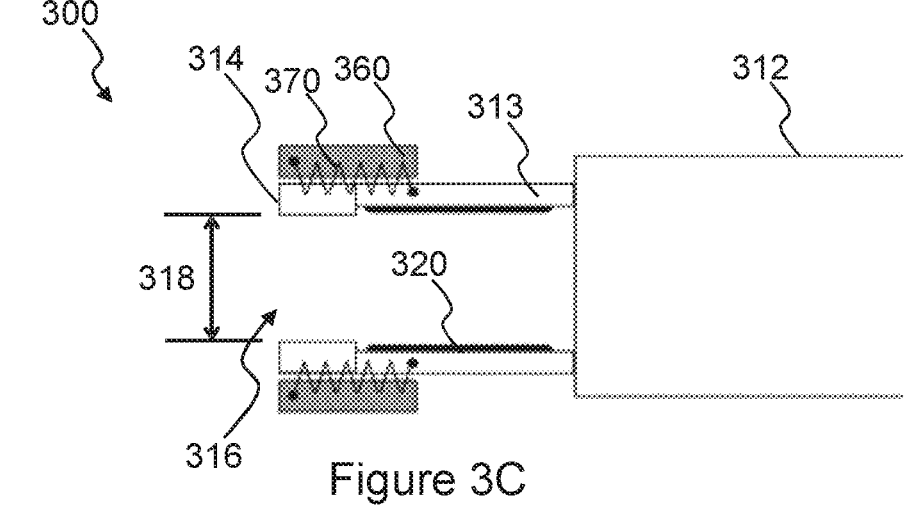
Figure 3D:
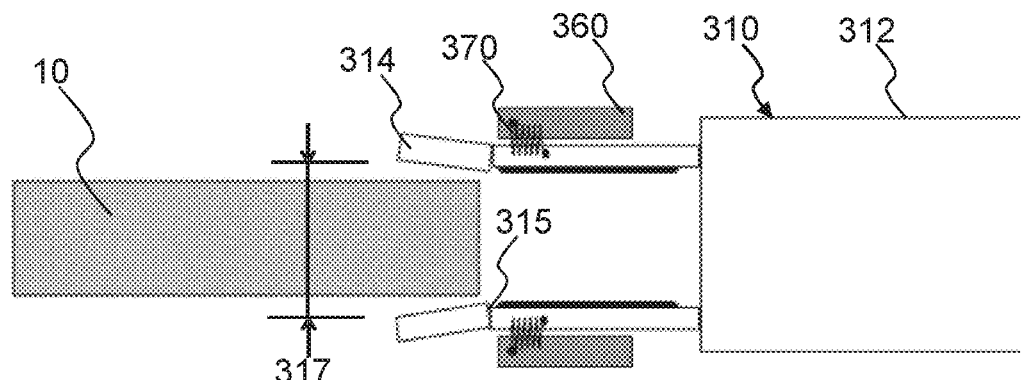
Figure 3E:
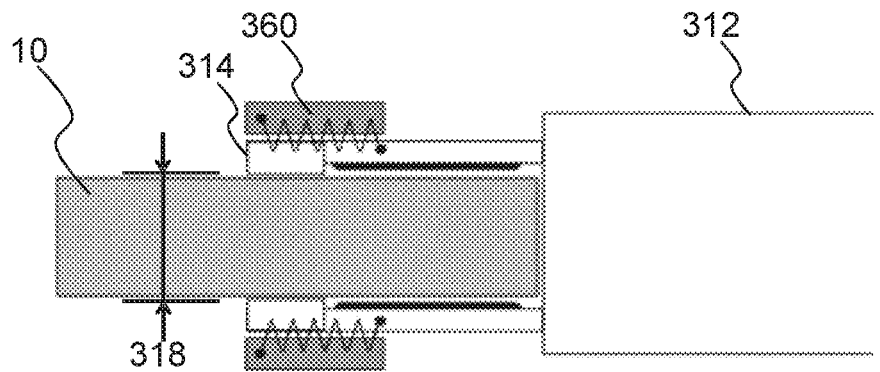

The moveable wall 114 is resilient and fixed to the main body 112 such that the open end of the cavity 116 has a first minimum diameter 117 when the moveable wall 114 is in the first position, as shown in FIG. 1E. As the moveable wall 114 is resilient, it can be deflected elastically relative to the main body 112 in order to change the diameter of the open end of the cavity 116, before returning to its first position automatically under the action of its own restoring force when the deflecting force is removed.

The collar 160 and the moveable wall 114 are sized such that the moveable wall 114 is undeflected by the collar 160 when the collar 160 is in the open position and is deflected radially inwardly by the collar 160 when the collar 160 is moved towards the constricting position. Thus, when the constricting member 160 is in the open position, the moveable wall 114 is in the first position, as shown in FIG. 1E, and when the constricting member 160 is in the constricting position, the moveable wall 114 is deflected to a second position in which the open end of the cavity 116 has a second minimum diameter 118, as shown in FIGS. 1D and 1F. The second minimum diameter 118 is smaller than the first minimum diameter 117. The collar 160 is thus operable to selectively constrict the open end of the cavity 116 by deflecting the moveable wall 114 to its second position.

With reference to FIGS. 1D to 1F, use of the device 100 will be described.

As shown in FIG. 1D, in its initial state, the collar 160 is biased towards its constricting position by the spring 170 and the moveable wall 114 is deflected to its second position by the collar 160. The open end of the cavity 116 is thus constricted by the moveable wall 114 and the collar 160 when the collar 160 is in the constricting position.

To insert an aerosol-generating article 10 into the cavity 116, the collar 160 is slid by a user against the action of the spring 170 and towards the downstream end of the device to its open position, as shown in FIG. 1E. In this position, the collar 160 is partially received within the recess 119 and no longer deflects the moveable wall 114 inwardly. Consequently, the moveable wall 114 automatically returns to its first position. The open end of the cavity 116 is thus enlarged when the collar 160 is in its open position. This expansion of the open end of the cavity 116 makes it easier for the user to insert the article 10 into the device 100. The article 10 is then inserted into the cavity such that the aerosol-forming substrate of the aerosol-generating article 10 is penetrated by the heating blade 120.

Once the article 10 has been fully inserted into the cavity 160, the collar 160 is released by the user, allowing the spring 170 to automatically return the collar 160 to the constricting position and, in turn, to deflect the moveable wall 114 to its second position, as shown in FIG. 1F. The moveable wall 114 and the collar 160 are sized such that the second minimum diameter 118 is the same as or less than the outer diameter of the aerosol-generating article. Thus, the aerosol-generating article 10 is automatically gripped within the cavity 116 by the moveable wall 114. This reduces the risk of accidental dislodgement of the article 10 within the cavity 116, allowing the relative position of the aerosol-generating article 10 and the heater 120 to be maintained for consistent aerosol characteristics.

When the article 10 has been consumed it may be removed either by pulling it from the cavity 116 with the collar 160 in the constricting position, or by moving the collar 160 to its open position to enlarge the open end of the cavity 116, allowing the article 10 to be pulled from the cavity 116 more easily.

With reference to FIGS. 2A to 2E, an electrically heated aerosol-generating device 200 according to a second embodiment of the present invention is shown. The aerosol-generating device 200 of the second embodiment is similar in construction and operation to first embodiment of aerosol-generating device 100 shown in FIGS. 1B to 1F, and where the same features are present, like reference numerals have been used. However, the electric heater in the second embodiment of aerosol-generating device 200 is an external heater, comprising a plurality of heating elements 220 arranged on an inner surface of the moveable wall 214 such that the heating elements 220 are around the periphery of the cavity 216. With this arrangement, the heating elements 220 are positioned outside the aerosol-forming substrate of the aerosol-generating article 10 when received in the cavity 216. In this example, the heating elements 220 extend along the length direction of the aerosol-generating device 200 and are spaced apart in the circumferential direction, around the inner surface of the moveable wall 214. With this arrangement, the heating elements are arranged perpendicularly to the direction of deflection of the moveable wall 214. This may reduce the force required to deflect the heating elements when deflecting the moveable wall relative to arrangements in which, for example, the heating elements extend in a hoop around the circumference of the cavity. However, it will be appreciated that other arrangements of external heater are envisaged and may be suitable.

With reference to FIGS. 2C to 2E, use of the device 200 will be described.

As shown in FIG. 2C, in its initial state, the collar 260 is biased towards its constricting position by the spring 270 and the moveable wall 214 is deflected to its second position by the collar 260. The open end of the cavity 216 is thus constricted by the moveable wall 214 and the collar 260 when the collar 260 is in the constricting position.

To insert an aerosol-generating article 10 into the cavity 216, the collar 260 is slid by a user against the action of the spring 270 and towards the downstream end of the device to its open position, as shown in FIG. 2D. In this position, the collar 260 is partially received within the recess 219 and no longer deflects the moveable wall 214 inwardly. This allows the moveable wall 214 to automatically return to its first position. The open end of the cavity 216 is thus enlarged when the collar 260 is in its open position. This expansion of the open end of the cavity 216 makes it easier for the user to insert the article 10 into the device 200. The article 10 is then inserted into the cavity until the downstream end of the article 10 reaches the downstream end of the cavity 216.

Once the article 10 has been fully inserted into the cavity 260, the collar 260 is released by the user, allowing the spring 270 to automatically return the collar 260 to the constricting position and, in turn, to deflect the moveable wall 214 to its second position, as shown in FIG. 2E. The moveable wall 214, the heating elements 220 and the collar 260 are sized such that the second minimum diameter 218 is the same as or less than the outer diameter of the aerosol-generating article 10. Thus, the aerosol-generating article 10 is automatically gripped within the cavity 216 when the collar 260 is released by the user. This reduces the risk of accidental dislodgement of the article 10 within the cavity 216, allowing the relative position of the aerosol-generating article 10 and the heater 220 to be maintained. Additionally, as the heating elements 220 are positioned on the inner surface of the moveable wall 214, the heating elements 220 are pressed against the aerosol-generating article 10 by the moveable wall 214 when the collar 260 is in the constricting position. This may help to improve heat transfer from the heating elements 220 to the aerosol-forming substrate of the aerosol-generating article 10 for consistent aerosol characteristics.

When the article 10 has been consumed it may be removed either by pulling it from the cavity 216 with the collar 260 in the constricting position, or by moving the collar 260 to its open position to enlarge the open end of the cavity 216, allowing the article 10 to be pulled from the cavity 216 more easily.

With reference to FIGS. 3A to 3E, an electrically heated aerosol-generating device 300 according to a third embodiment of the present invention is shown. The aerosol-generating device 300 of the third embodiment is similar in construction and operation to second embodiment of aerosol-generating device 200 shown in FIGS. 2A to 2E, and where the same features are present, like reference numerals have been used. However, in the third embodiment of aerosol-generating device 300, the moveable wall 314 defines only an upstream end of the cavity 316. The remainder of the cavity 316 is defined by a stationary wall 313 which is fixed to the main body 312 of the housing 310. The moveable wall 314 is connected to the stationary wall 313 at a hinge 315. In this example, the stationary wall 313 and the moveable wall 314 are integral and the hinge 315 is formed from a region of the housing having reduced thickness which allows the moveable wall 314 to pivot relative to the stationary wall 313 by elastic deformation at the hinge 315. In other examples, the stationary wall 313, moveable wall 314, and hinge 315 may be separate components. Unlike in the second embodiment of aerosol-generating device 200, in the third embodiment of aerosol-generating device 300, the plurality of external heating elements 320 are arranged on an inner surface of the stationary wall 313, rather than on the moveable wall 314. Additionally, as the moveable wall 314 is located only at the upstream end of the cavity 316, the collar 360 can be shorter, as shown in FIGS. 3A to 3E. Consequently, the third embodiment of aerosol-generating device 300 does not have a recess into which the collar 360 is received when in the open position. Instead, the collar 360 remains upstream of the main body 312 and slides over the outside of the stationary wall 313 and the moveable wall 314. In view of this, the spring 370 is fixed to the stationary wall 313, rather than in the main body 312 as with the first and second embodiments. Nevertheless, the spring 370 is still positioned between the collar 360 and the housing 310. Although the collar 360 is shorter than in the first and second embodiments, this is not essential. Instead, in other examples, the collar may have a length which is the same as, or greater than, the length of the collar in the first and second embodiments and may be received in a recess in the main body of the housing, or slidable over the outer surface of the main body.

The specific embodiments and examples described above illustrate but do not limit the invention. It is to be understood that other embodiments of the invention may be made and the specific embodiments and examples described herein are not exhaustive.

The invention claimed is:

1. An aerosol-generating device, comprising:
   a housing defining a cavity configured to receive an aerosol-generating article, the cavity having an open end through which the aerosol-generating article is receivable into the cavity; and a constricting member connected to the housing, wherein the constricting member is moveable between an open position and a constricting position, which selectively constricts at least a portion of the cavity; and
   an electric heater disposed in the cavity and being configured to heat an aerosol-forming substrate when the aerosol-generating article is received in the cavity, wherein the electric heater comprises one or more external heating elements,
   wherein the plurality of external heating elements are arranged on an inner surface of a moveable wall of the housing.

2. The aerosol-generating device according to claim 1, wherein the external heating elements extend along a longitudinal direction of the cavity.

3. The aerosol-generating device according to claim 1,
   wherein the housing comprises a main body and the moveable wall is connected to the main body, the moveable wall defining at least part of the open end of the cavity,
   wherein the moveable wall is moveable between a first position in which the open end has a first diameter and a second position in which the open end has a second, smaller diameter, and
   wherein the constricting member is arranged to selectively constrict the open end of the cavity by deflecting the moveable wall to the second position.

4. The aerosol-generating device according to claim 3, wherein the moveable wall is biased towards the first position when the constricting member is in the open position.

5. The aerosol-generating device according to claim 3, wherein the moveable wall is connected to the main body of the housing by a hinge about which the moveable wall is moveable between the first and second positions.

6. The aerosol-generating system, comprising:
   an aerosol-generating device according to claim 1;
   and an aerosol-generating article for the aerosol-generating device, the aerosol-generating article comprising an aerosol-forming substrate.

7. The aerosol-generating system according to claim 6, wherein the aerosol-forming substrate comprises a tobacco-containing material comprising volatile tobacco flavour compounds which are released from the substrate upon heating.

8. The aerosol-generating system according to claim 6, further comprising a user interface configured to activate the aerosol-generating system.

* * * * *